United States Patent
Callede et al.

(10) Patent No.: US 9,901,326 B2
(45) Date of Patent: Feb. 27, 2018

(54) DEVICE FOR TAKING AT LEAST ONE SAMPLE OF TISSUE

(71) Applicant: COLOPLAST A/S, Humlebaek (DK)

(72) Inventors: David Callede, Sarlat la Caneda (FR); Laurent Pivard, Dortan (FR); Denis Pinaud, Draillant (FR); Fabrice Teppe, Oyonnax (FR); Adrien Moine, Evian (FR)

(73) Assignee: Coloplast A/S, Humlebaek (DK)

( * ) Notice: Subject to any disclaimer, the term of this patent is extended or adjusted under 35 U.S.C. 154(b) by 0 days.

(21) Appl. No.: 14/369,200

(22) PCT Filed: Jan. 11, 2013

(86) PCT No.: PCT/EP2013/050455
§ 371 (c)(1),
(2) Date: Jun. 27, 2014

(87) PCT Pub. No.: WO2013/107692
PCT Pub. Date: Jul. 25, 2013

(65) Prior Publication Data
US 2015/0018713 A1    Jan. 15, 2015

(30) Foreign Application Priority Data
Jan. 16, 2012  (EP) .................... 12290017

(51) Int. Cl.
*A61B 10/02* (2006.01)
(52) U.S. Cl.
CPC ...... *A61B 10/0266* (2013.01); *A61B 10/0275* (2013.01); *A61B 2010/0208* (2013.01)
(58) Field of Classification Search
CPC .................... A61B 10/0275; A61B 2010/0208
See application file for complete search history.

(56) References Cited

U.S. PATENT DOCUMENTS

| 5,538,010 A | 7/1996 | Darr et al. |
| 5,842,999 A | 12/1998 | Pruitt et al. |

(Continued)

FOREIGN PATENT DOCUMENTS

| WO | 2009137288 A2 | 11/2009 |
| WO | 2011018091 A1 | 2/2011 |

*Primary Examiner* — Daniel Cerioni
*Assistant Examiner* — Yasmeen S Warsi
(74) *Attorney, Agent, or Firm* — Coloplast Corp., Coloplast A/S; Nick Baumann

(57) ABSTRACT

This invention relates to a device (10) for taking at least one sample of soft tissue from an organ, said device comprising a body (11) and a needle (12) formed by a stylet and a cannula coaxial with said stylet. The device comprises a mechanism for arming the needle, designed for sequentially moving the cannula and then the stylet from a rest position wherein the stylet and the cannula are extended towards the outside of the body, to a shooting position wherein the stylet and the cannula are retracted towards the rear of the body, and a triggering mechanism designed to release the stylet then the cannula and to allow their displacement from the shooting position to the rest position. The cannula is kinematically coupled to a cannula slider (24) comprising at least one retaining element (26) for maintaining the cannula slider in a shooting position. The stylet is coupled kinematically to a stylet slider (30) comprising at least one retaining element (32) for maintaining the stylet slider in a shooting position and means for unlocking the cannula slider. This device is characterized in that the needle (12) comprises at least one sliding shoe (50) located on the side of the body of the device (11) and arranged in such a way that the stylet (13) and the cannula (14) slide relative to each other while at the same time resting on this sliding shoe (50).

14 Claims, 2 Drawing Sheets

(56) References Cited

U.S. PATENT DOCUMENTS

2004/0068231 A1* 4/2004 Blondeau ........... A61B 10/0275
                                                    604/157
2005/0080355 A1   4/2005 Mark
2005/0182394 A1   8/2005 Spero
2006/0293612 A1* 12/2006 Jenson ............... A61B 17/3207
                                                    600/585

* cited by examiner

DEVICE FOR TAKING AT LEAST ONE SAMPLE OF TISSUE

TECHNICAL FIELD

The present invention relates to a device for taking at least one sample of soft tissue from an organ, said device comprising a body and a needle formed by a stylet and a cannula coaxial with said stylet, said device comprising a mechanism for arming the needle, designed for sequentially moving the cannula and then the stylet from a rest position wherein the stylet and the cannula are extended towards the outside of the body, to a shooting position wherein the stylet and the cannula are retracted towards the rear of the body, and a triggering mechanism designed to release the stylet then the cannula and to allow their displacement from the shooting position to the rest position, the cannula being coupled kinematically to a cannula slider comprising at least one retaining element for maintaining the cannula slider in a shooting position, the stylet being coupled kinematically to a stylet slider comprising at least one retaining element for maintaining the stylet slider in a shooting position and means for unlocking the cannula slider.

BACKGROUND ART

Nowadays, there are several devices for taking samples of soft tissue, these devices being generally used to extract, in a minimally invasive way, a sample of an organ from a human or an animal for analysis purpose. This extraction operation is generally known as biopsy and the used device is known as a biopsy gun.

Such a sampling device comprises in particular a sampling needle formed by a cannula and a stylet, an arming mechanism placed on a body and a trigger also placed on the body of the device.

The arming mechanism is used to partially retract the needle towards the inside of the body of the device, the device is placed near the organ from which one wishes to take a sample, then the trigger is pressed so that the needle can penetrate into the organ. The needle being formed by a stylet and by a cannula, the stylet penetrates into the organ, the cannula then covers the stylet. This stylet comprises at least one notch receiving the tissue to be taken. When the cannula covers the stylet, the tissue sample is trapped in the notch and is cut. The unit is withdrawn so that the sample(s) arranged between the stylet and the cannula can be taken. An example of application of such a device is taking tissues of the prostate.

The arming of the needle is generally achieved in two phases, namely the arming of the cannula in a first phase and the arming of the stylet in a second phase.

During sampling of tissues, it is frequent that the person who carries out the sampling has only one free hand, the other hand being used to hold other medical devices such as for instance an echographic probe. In this case, it is important to be able to manipulate the sampling device with one single hand. The manipulation implies here the arming of the cannula, the arming of the stylet and the release of the shot allowing for the sample to be taken.

Among the existing devices, which enable manipulation with one single hand, one of them is described in the U.S. Pat. No. 7,153,275. This device is perfectly functional in most cases. However, problems may occur in certain circumstances. These problems can come from the fact that the stylet and the cannula are not perfectly aligned and that the stylet does not slide in a totally optimal way in the cannula. Indeed, an optimal sliding motion involves particularly tight manufacturing tolerances for the realisation of the parts of the biopsy gun. These tolerances can sometimes be difficult to maintain on parts made from plastic. This can lead to jamming of the needle, sometimes even to deformation of the latter. This has also as a consequence that the number of shots that it is possible to carry out with a device is reduced.

In order to minimise the problems linked to the jamming of the stylet in the cannula, a relatively powerful spring is foreseen for the cannula in order to propel the latter in an effective way. This has the drawback that a greater force is necessary to arm the device, which is unpleasant for the user. Despite such a spring, the needle may jam and bend so that the device becomes unusable.

This invention proposes to realize a tissue sampling device which has the advantages of the devices of the prior art i.e. it is possible to use this device with one hand. However, this device does not have the drawbacks of the systems of the prior art. Thus, the risk of jamming of the needle, as well as the risk of breakage or deformation, is strongly reduced or even eliminated.

Furthermore, and especially in implementations of the invention wherein the sampling device may be a single-use sampling device, particularly the risk of jamming of the needle and/or the cannula individually or in relation to each other is reduced or eliminated. This is at least partly because the sampling device, and particularly the movable parts thereof e.g. the needle and the cannula, is then assembled correctly during manufacture leaving no risks of a user putting the parts together in the wrong manner as could very well be the case with re-useable sampling devices. In addition, a single-use device is also significantly less prone to risks of contamination, e.g. by bacteria on a user's hands.

Moreover, as a single-use sampling device may enable production tolerances different from those of a re-useable sampling device, it is in most cases less costly to manufacture than such re-useable sampling devices. Thereby, the improved security mechanisms against unintentional firing of the sampling device according to the different implementations of the invention may be particularly, but not exclusively, suitable for single-use sampling devices in order to meet any potential risks due to such different production tolerances as mentioned above.

DISCLOSURE OF THE INVENTION

The object of the invention is fulfilled by a sampling device as defined in the preamble and characterized in that the needle comprises at least one sliding shoe located on the side of the body of the device and arranged in such a way that the stylet and the cannula slide relative to each other while at the same time resting on this sliding shoe.

According to the present invention, the device for taking samples can easily be manipulated with one hand. For this scope, it comprises a body having an essentially cylindrical shape that can be easily held. It also comprises a sliding arming button, which is positioned on the body so that this button can be easily moved using one finger. This arming button is connected to an arming mechanism, which has two different functions. In a first phase, the displacement of the arming button has the effect of moving the cannula towards the back of the body. When this displacement to a certain position has been achieved, the arming button is released, allowing it to go back to its initial position. When it is operated again, the arming button has another function with respect to the previous one. In fact it is used to move the stylet towards the back of the body. Thanks to the mechanism of the invention, the user carries out the same displacement movement of the arming button twice, these two movements having different effects.

This way of proceeding has the advantage of enabling the realization of a body of relatively small length and of ensuring a stroke of the arming button, which is compatible with the displacement of the user's finger, without obliging the user to change the position of his/her hand.

The cannula and the stylet are made in such a way that the stylet is guided by the cannula while the friction is significantly limited between the elements.

The device of the invention enables to avoid the jamming of the stylet and the cannula, as well as the possible consequences of it, such as deformation or rupture.

By virtue of the geometry of the device, the elements which enable the guidance of the stylet and the cannula, as well as the propulsion and retaining elements for the stylet and the cannula are arranged symmetrically around a longitudinal axis materialized by the stylet. This ensures that there are few transversal forces. Such transversal forces have the effect of increasing the friction between the parts, of causing wear and of risks of rupture as well as of jamming. By suppressing these transversal forces, it is possible to use smaller springs as it is no longer necessary to fight against friction. The biopsy gun is thus easier to use since the arming is made easier. Moreover, the gun can be used more often since the jamming risk is reduced.

BRIEF DESCRIPTION OF THE DRAWINGS

This invention and its advantages will be better understood with reference to the enclosed drawings and to the detailed description of a particular embodiment, in which.

BEST MODE FOR CARRYING OUT THE INVENTION

Figure 1:
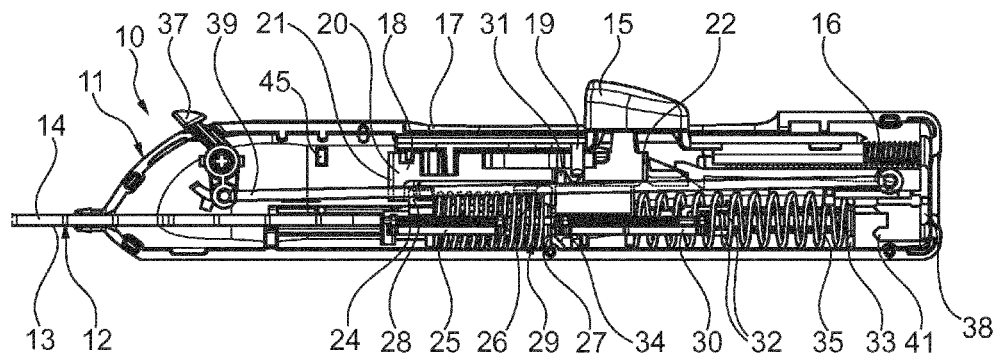
FIG. 1 is an overview of the device of the present invention.

With reference to the drawings, the sampling device 10 according to this invention essentially comprises a body 11 and a needle 12. The needle is formed by a stylet 13 and by a cannula 14. The stylet comprises a tip allowing a penetration of the needle into the organ from which one wishes to take a sample. Furthermore, this stylet comprises at least one notch (not represented). In practice, the stylet 13 comprises a relatively long notch that enables a sample of great length to be taken. The cannula 14 slides around the stylet 13 and is used on one hand to section the tissue into which the stylet has penetrated and on the other hand to keep in place the tissues taken at the time of the extraction of the needle from the organ.

The body 11 essentially comprises an arming mechanism arranged to arm the needle 12 and a triggering device arranged to release a shot of the needle for the intended sampling. More particularly, the arming of the needle is carried out in two phases, namely a phase of arming the cannula 14 and a phase of arming the stylet 13.

The sampling is made by a shot of the needle. Such a shooting also comprises two phases, namely a displacement phase of the stylet 13 under the effect of a propelling power of the stylet, then a displacement phase of the cannula 14 under the effect of a propelling power of the cannula. Releasing a shot is achieved by liberating the displacement of the stylet. The displacement of the cannula is a consequence of the release of the stylet as it will be explained in detail below.

In practice, the mechanism for arming the cannula and the mechanism for arming the stylet use only one arming button 15 which acts differently depending on whether the arming of the cannula has already been carried out or not. This arming button cooperates with a return spring 16 of the arming button, this spring having the function to bring back the arming button 15 to the rest position i.e. towards the front of the body, when it is not manipulated.

The body of the device is formed by two parts which, once assembled, comprise guidance grooves intended to ensure the displacement of the parts. The body also comprises a slit 17 in which the arming button moves.

With reference to the figures, the arming button 15 cooperates with a platform 18. This platform can pivot around a platform axis 19 integral with the arming button. One of the ends of the platform, located near the front end of the sampling device i.e. the needle-end of the sampling device, comprises a widened zone 20, each end of this widened zone including a finger 21 whose function is described in detail below. The rear end of the platform comprises a pushing device 22 whose function is also described in detail below.

The platform 18 is connected to the arming button 15 by the platform axis 19 and by a return device (not represented) that can be in particular a spring or an elastic tab and which has the function of keeping this platform in a predefined position called a rest position.

The mechanism for arming the cannula 14 is intended to move the cannula into the shooting position. This cannula is coupled to a cannula slider 24. According to one advantageous embodiment, the cannula slider 24 comprises two fins 25 disposed in a plane containing also the cannula. These two fins 25 cooperate with two guide grooves realized in the body of the device so as to ensure an effective sliding motion of the cannula slider 24. This slider comprises, at its rear end, a retaining element 26 of the cannula slider. According to an advantageous embodiment, the retaining element is formed by two hooks. Advantageously, these hooks are symmetrical and realized so as to have a certain flexibility, which allows for them to be hooked onto a retaining device 27 of the cannula slider and to be unhooked from this device by approaching the hooks to each other. It is also possible to use only one hook, or several hooks arranged asymmetrically.

Furthermore, the cannula slider 24 comprises a spur 28 cooperating with one of the fingers 21 of the platform. The cannula slider cooperates with a spring 29 for the propulsion of the cannula slider, which is arranged between the cannula slider 24 and the retaining device 27 of the cannula slider. This spring 29 is designed to supply the required force to propel the cannula slider towards the front of the body. The displacement of the cannula slider towards the back of the body effects the compression of this spring.

The mechanism for arming the stylet is intended for the displacement of the stylet 13 into the shooting position, this displacement being achieved after the cannula 14 has been armed. To that effect, the stylet 13 is kinematically coupled to a stylet slider 30. This stylet slider can comprise two parts, namely a support device and a guide device. The support device is integral with the stylet 13. According to a particular embodiment, it is overmolded on this stylet. The guide device comprises fins cooperating with guide grooves realized in the body 11 of the device. The guide device has a configuration such that the displacement of the guide device leads to the displacement of the support device. However, these two elements present a certain clearance between them. This clearance enables a relative displacement of the support device in comparison with the guide device in a plane substantially perpendicular to the needle. In principle, little or no clearance at all exists in a longitudinal axis in comparison with the needle. This clearance enables to take into account the manufacturing tolerances of the different elements of the device of the invention. The support device is in a "suspended" setup in comparison with the guide device.

This guiding device comprises a spur 31 near its front end and a retaining element 32 at its rear end. Like for the cannula slider, the retaining element 32 can be formed by two partially elastic hooks. It can also be formed by only one hook, or by several hooks arranged symmetrically or asymmetrically.

This retaining element 32 can be hooked on a retaining device 33 of the stylet slider and can be unhooked from this device by approaching the hooks to each other.

Like for the cannula slider, the hooks of the stylet slider are sufficiently flexible to be able to be deformed one towards the other and sufficiently rigid to be able to be maintained on an adequate support.

The stylet slider 30 comprises, at its front end i.e. at the side of the cannula slider, unlocking means 34 formed for instance by two inclined planes.

The guide device of the stylet slider cooperates with a spring 35 for the propulsion of the stylet slider, which is placed between the stylet slider 30 and the retaining device 33 of the stylet slider. This spring is designed to supply the required force to propel the stylet slider 30 towards the front of the body and to unlock the cannula slider. The displacement of the stylet slider towards the back of the body effects the compression of this spring.

The device according to this invention further comprises a triggering device. According to an advantageous embodiment, this triggering device comprises two triggers 37, 38 connected together by a rod 39. One trigger 37 is placed in the front of the body, in front of the arming button 15, and the other trigger 38 is placed in the rear of the body. The rear trigger 38 is associated with a return spring of the trigger, designed to bring the trigger back in the original position after it has been pressed.

The rear trigger 38 comprises means for unlocking 41 the stylet slider formed by two elements arranged in inclined planes.

In the device for taking samples according to the invention, the needle 12 comprises a sliding shoe 50 placed between the cannula 14 and the stylet 13. The function of this sliding shoe 50 is to ensure a guidance of the stylet with respect to the cannula while limiting friction.

Unlike the conventional devices in which friction between the stylet and the cannula occur along the entire length of the needle, in the device according to the invention friction is present only in the sliding shoe. On the one hand, the friction area is short and on the other hand, the material forming this shoe can be selected so as to minimize friction.

Figure 2:
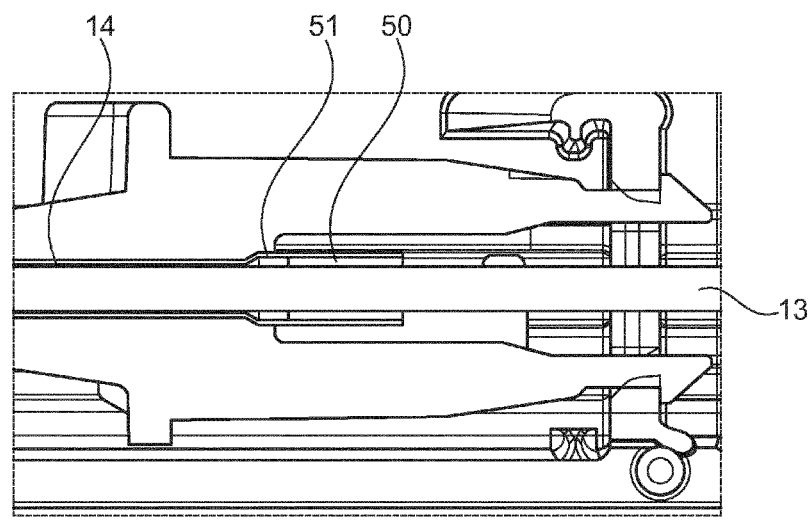
FIG. 2 shows a first embodiment of a detail of the invention.

With reference to the embodiment shown in FIG. 2, the cannula 14 comprises a flared area 51 located on the side of the body of the device. The sliding shoe 50 is integral with the cannula and is located in this flared area. This sliding shoe comprises a bore in which the stylet 13 slides.

The relative sizes of the cannula 14, of the stylet 13 and of the sliding shoe 50 are such that the stylet is guided and undergoes friction essentially in the sliding shoe. Apart from this, there is virtually no friction between the cannula and the stylet.

It is possible to choose a material for the sliding shoe so as to obtain a very low friction coefficient with the cannula. Thus, loss of speed related to friction is minimized.

Figure 3:
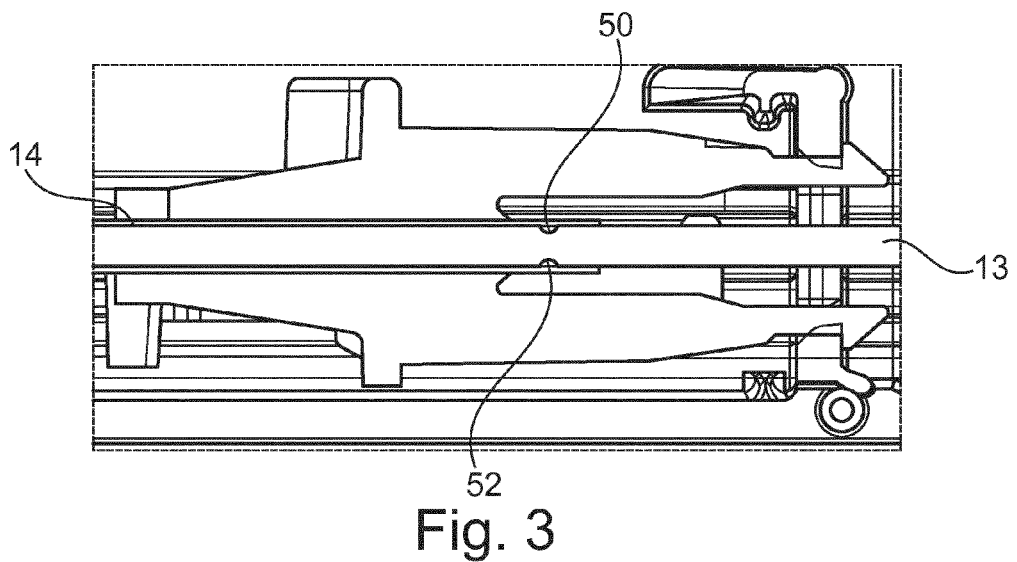
FIG. 3 is a cross section of a second embodiment of the detail of the invention shown in FIG. 2.

In the embodiment shown in FIG. 3, the stylet 13 comprises a groove 52 while the cannula 14 has a significantly constant cross section. The sliding shoe 50 is located in this groove 52 of the cannula. According to an advantageous embodiment, the sliding shoe is formed by a synthetic material moulded in said groove. Advantageously, this sliding shoe slightly exceeds the stylet 13 in such a way that the material that forms this shoe is in contact with the cannula while the rest of the stylet has a little contact or no contact with the cannula.

Figure 4:
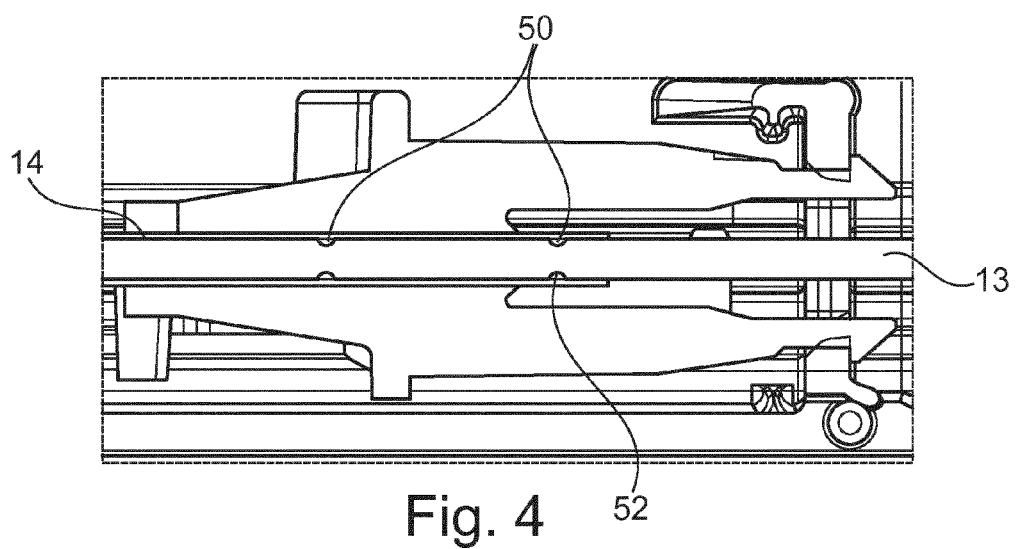
FIG. 4 shows a variant of the embodiment of FIG. 3.

In the embodiment of FIG. 4, the stylet 13 comprises several grooves 52. These grooves receive the sliding shoe 50. The latter is thus formed by several sections arranged along the needle. This embodiment has the advantage of allowing guidance on a relatively large area, without the necessity of a significant weakening of the section of the stylet. Indeed, this section is only weakened in order to carry out the grooves 52.

It should be noted that it is possible to carry out more than two grooves and to distribute them along the stylet.

Figure 5:
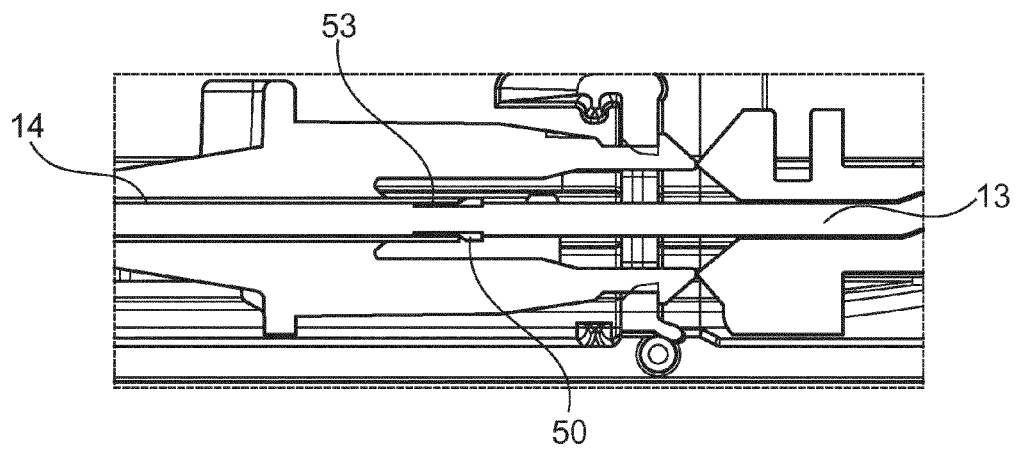
FIG. 5 shows an additional embodiment of the detail of the invention of FIG. 2.

In the embodiment disclosed in FIG. 5, the stylet 13 comprises a recess 53 arranged on the rear side of the body. The sliding shoe 50 is partially arranged in this recess 53 and partially arranged around the stylet. The part of the sliding shoe 50 located outside the recess has a larger dimension than the inside dimension of the cannula. As a result this larger dimension part is used as stop and centering for the cannula.

The sampling device according to this invention operates in the following way. Let us assume that the initial position is a position in which the cannula 14 and the stylet 13 are maximally extended towards the outside of the body 11 of the device. This position corresponds to the normal position of the device when it is not going to be used, i.e. rest position.

In a first phase, the arming of the cannula 14 is carried out. During this operation, the user actuates the arming button 15, making it slide towards the back of the device 10. The platform 18 being integral with the arming button 15, the displacement of the latter also draws the platform backwards. One of the fingers 21 of the platform 18 comes in contact with the spur 28 placed towards the front end of the cannula slider 24. The latter is thus displaced backwards, in opposition to the force of the spring 29 for the propulsion of the cannula slider. This movement is carried out until the retaining elements 26 of the cannula slider 24 enter into contact with the retaining device 27 of the cannula slider. This retaining device 27 is for instance a ring realized in the body of the device. The ring comprises a central hole in which the ends of the hooks of the cannula slider pass. These hooks lean on the back face of the ring and maintain the cannula slider 24 in opposition to the force of the propulsion spring of this cannula slider.

When the arming of the cannula is terminated, the arming button 15 is released. It returns to its initial position towards the front of the device, under the effect of the return spring 16 of the arming button.

During the forward displacement of the platform 18, following the forward displacement of the arming button 15, a ramp of the platform comes into contact with a plug 45 realized in the body. This ramp has the effect of rotating the platform 18 around the platform axis 19, against the force of the return device 23 of the platform. It should be noted that according to the chosen practical realization, it is also possible to provide for the return device of the platform to be constrained before the arming of the cannula and to be liberated when the arming of the cannula is terminated.

For the arming of the stylet 13, the arming button 15 is displaced backwards again. However, the platform 18 is no longer in the initial position. Indeed, the latter has pivoted around the platform axis 19, as the ramp of the platform has been displaced by the support against the plug 45. By this rotation, the finger 21 of the platform does not, on one side, come into contact with the spur 28 of the cannula slider and, on the other side, the pushing device 22 of the platform presses against the spur 31 of the guiding device of the stylet slider. Thus this slider is moved towards the back of the device, in opposition to the force of the spring 35 of propulsion of the stylet slider, until the retaining elements 32 of the support device of the stylet slider are arranged in the retaining device 33 of the stylet slider. This retaining device is similar to the retaining device 27 of the hooks of the cannula slider. It has thus advantageously an annular form with a hole in which the hooks of the stylet slider come to lie. It should be noted that the retaining element of the stylet slider could be realized on the guide device instead of being realized on the support device. Likewise, the index could rest on the support device in place of the guide device, as long as the displacement of the support device leads to the displacement of the guide device.

At this stage, the device is triggered out and ready for the shot. The device is stable in the sense that the cannula and stylet slider hooks are maintained against the corresponding retaining elements. The arming button 15 is released and returns to its initial position under the effect of the return spring of the arming button. The platform 18 also returns to its initial position.

When the needle is armed, the sampling is started by a shot. This shot can be started by means of one of the triggers 37, 38 which have the function of releasing the displacement of the stylet and the cannula by releasing the stylet slider 30. The stylet slider is first propelled towards the front of the body under the force of the spring 35 of stylet propulsion. During this propulsion, the fins of the guide device follow the guide grooves realized in the body of the device. The displacement of the guide device leads to the displacement of the support device. The stylet 13 is guided by the cannula 14 with a small clearance in a plane perpendicular to the displacement direction of the needle. This clearance enables to take into account the manufacturing tolerances of the different elements of the device of the invention.

The cannula slider 24 is then propelled towards the front of the device under the force of the spring 29 for cannula propulsion.

During this shot, the relative sliding of the cannula and of the stylet is achieved while they essentially rest on the sliding shoe 50. This shoe being achieved in order to optimize friction, the shot can be triggered with a minimum loss of energy. The shooting speed is thus improved, thus improving the quality of the samples that are taken. The risk of jamming is also minimized.

In the disclosed embodiment, the triggering mechanism comprises the two triggers and the rod 39 previously mentioned. The feature of having one of the triggers arranged in front of the body, in front of the tensioning button and the other arranged in the rear of the body enables the user to easily access the triggering mechanism, whatever is the position of the hand during the use of the device.

According to an advantageous embodiment, a security mechanism is provided for preventing a shot during an involuntary manipulation of one of the triggers and in particular of the front trigger. Before the release of the shot, it is necessary to laterally displace this front trigger 37 in relation to the body 11 in order to remove the security function of the mechanism. After the shot, it is necessary to laterally re-displace the front trigger 37 in order to reactivate the security function. This security function is manual in the sense that the user has the choice whether to activate the function by displacing the trigger or not.

To release the shot, it is necessary to press one of the triggers 37, 38, the front or the rear one. Actually, in the disclosed embodiment, the shot is always released by a displacement of the rear trigger 38. However, the front trigger and the rear trigger being linked by the rod 39, a pressure on the front trigger has as result to move the rear trigger forward under the pressure of the rod. Thus the mechanism can be used by pressing either the rear trigger or the front trigger.

When the rear trigger 38 is pressed, the unlocking means 41 being part of the rear trigger (or means for unlocking the stylet slider) comes into contact with the hooks of the stylet slider and displaces them towards each other. In this way, they are released from the retaining device 33 of the stylet slider. This slider 30 is propelled forward under the effect of the propulsion spring 35 of the stylet slider.

The means 34 for unlocking the cannula slider comes into contact with the hooks of the cannula slider, presses these hooks towards the centre and releases the retaining elements 27 of the cannula slider. The cannula slider 24 advances under the effect of the propulsion spring 29 of the cannula. This slider advances until it arrives at a stop realized in the body of the device. At this stage, the shot is terminated and the device can be withdrawn from the organ from which samples have been taken.

After the arming of the stylet, the platform 18 has returned to its rest position under the effect of the return device of the platform. After the shot, the pieces of the device return to their initial positions. The sample taken is confined between the stylet 13 and the cannula 14, in the notch provided for this purpose. This sample can be withdrawn by moving back the cannula, for instance by carrying out an arming movement as previously explained. When the arming of the cannula is terminated, it is possible to withdraw the sample. If a new sampling has to be carried out, the arming button is operated so as to arm the device totally and to make it ready for the shot. If it is not necessary to take a new sample, the arming is carried out as well and a blank shot is made.

The present invention has several advantages in comparison with the devices of the prior art. In particular, by the setup of the retaining elements 26, 32 of the stylet and cannula sliders, it is possible to provide at least two symmetrical hooks. The forces applied on these hooks to hold them by the retaining means as well as during their unhooking during a shot are symmetrical. On one hand, this ensures that there is no flexing and/or twist on the needle and on the other hand, this enables a safer support of the hooks.

The clearance between the guide device and the support device forming the stylet slider also ensures an optimal displacement of the stylet in relation to the cannula and thus prevents the jamming or deformation of the needle.

According to an advantageous realization, the needle is off-center towards the bottom of the device 10. This enables the use of the device in an easier way with another apparatus as for example an echographic probe.

The device according to the invention can be operated by one single hand since the arming of the cannula and the arming of the stylet use the same arming button.

By the symmetrical construction of the retaining elements of cannula and stylet sliders and by the position of the propulsion springs of these sliders, the stresses are divided symmetrically around the axis of the needle. Thus, the risks of jamming between the stylet and the cannula are minimized, which in some implementations of the invention enables the use of the device several times and thus allows for a greater number of samples to be taken.

The reduction of the risk of jamming, in particular thanks to the sliding shoe, and the realisation of the stylet slider in two elements that have a clearance among each other allows for the reduction of the force of the propulsion springs while maintaining a high displacement speed for the sliders. This is advantageous for the user because a smaller force is necessary for arming the device. The manipulation with a single hand is easier in this way.

Using guide grooves realized in the body of the device and slider fins moving in these grooves also ensures an optimal guidance and a diminution of the jamming risk.

The invention claimed is:

1. A sampling device for taking a sample of soft tissue from an organ, the sampling device comprising:
    a body and a needle oriented on a longitudinal axis of the body and of the sampling device, the needle formed by a stylet and a cannula coaxial with the stylet;
    an arming button for arming the needle, the arming button connected to a platform provided with a platform finger and a platform pusher, the platform finger to engage a cannula slider of the cannula and adapted to move the cannula to a shooting position, the platform is rotatable on a platform axis to a rotated position that engages the platform pusher with a stylet slider of the stylet such that subsequent movement of the platform pusher moves the stylet to the shooting position wherein the stylet and the cannula are retained in the shooting position with the stylet and the cannula retracted into the body of the sampling device; and
    at least one trigger adapted to release the stylet and the cannula from the shooting position;
    wherein the cannula is coupled kinematically to the cannula slider and the stylet is coupled kinematically to the stylet slider;
    wherein a sliding shoe is between an internal surface of the cannula and an external surface of the stylet and the sliding shoe is between a first portion of the stylet and the cannula and absent from between a second portion of the stylet and the cannula, wherein the second portion of the stylet is distal to the first portion of the stylet and the sliding shoe is adapted to guide the stylet with respect to the cannula and limit friction between the stylet and the cannula.

2. The sampling device according to claim 1, characterized in that the cannula comprises a flared area at its end located on a side of the body and the sliding shoe is arranged in this flared area and is integral with the cannula.

3. The sampling device according to claim 1, characterized in that the stylet comprises at least one groove and the sliding shoe is at least partially placed in this groove.

4. The sampling device according to claim 1, characterized in that the stylet comprises a recess and the sliding shoe is partially located in this recess.

5. The sampling device according to claim 1, wherein the at least one trigger includes a front trigger located proximal of the arming button and a rear trigger located distal of the arming button.

6. The sampling device according to claim 1, wherein the at least one trigger includes a front trigger located proximal of the arming button, and the front trigger is coupled to the stylet slider.

7. The sampling device according to claim 1, wherein the at least one trigger includes a rear trigger located distal of the arming button, and the rear trigger is coupled to the stylet slider.

8. The sampling device according to claim 1, wherein the at least one trigger includes a front trigger located proximal of the arming button and a rear trigger located distal of the arming button, and the front trigger and the rear trigger are both coupled to the stylet slider.

9. The sampling device according to claim 2, wherein the sliding shoe comprises a bore through which the stylet is adapted to slide relative to the cannula.

10. The sampling device according to claim 1, wherein the sliding shoe is arranged around a portion of the stylet.

11. The sampling device according to claim 3, wherein the sliding shoe is formed of a synthetic material molded in the groove.

12. The sampling device according to claim 3, wherein the stylet comprises a plurality of grooves distributed along the stylet.

13. The sampling device according to claim 1, wherein a first portion of the sliding shoe is arranged in a recess of the stylet and a second portion of the sliding shoe is arranged around the stylet.

14. The sampling device according to claim 13, wherein the second portion of the sliding shoe has an external cross-sectional dimension greater than an internal cross-sectional dimension of the cannula such as to provide a stop and centering for the cannula.

* * * * *